United States Patent [19]
Gastrock et al.

[11] 3,957,978
[45] May 18, 1976

[54] PHOSPHONIUM ANTI-PARASITICS

[75] Inventors: William Henry Gastrock, Hightstown; John Anthony Pankavich, Hamilton Square; Spencer Douglas Carter, Trenton, all of N.J.

[73] Assignee: American Cyanamid Company, Stamford, Conn.

[22] Filed: Feb. 14, 1975

[21] Appl. No.: 550,064

[52] U.S. Cl. .............................. 424/204; 260/438.1; 260/439 R; 260/606.5 P
[51] Int. Cl.² .......................................... A61K 31/66
[58] Field of Search .................. 424/204; 260/606.5

[56] References Cited
UNITED STATES PATENTS

| | | | |
|---|---|---|---|
| 3,262,971 | 7/1966 | Matthews | 260/606.5 |
| 3,374,256 | 3/1968 | Driscoll et al. | 260/606.5 |
| 3,437,473 | 4/1969 | Driscoll et al. | 424/204 |

*Primary Examiner*—V. D. Turner
*Attorney, Agent, or Firm*—Denis A. Polyn

[57] ABSTRACT

A method for controlling helminths in domestic and farm animals by administering to said animals anthelmintically effective amounts of phosphonium compounds, is described.

19 Claims, No Drawings

PHOSPHONIUM ANTI-PARASITICS

SUMMARY OF THE INVENTION

This invention relates to a method for controlling helminths in domestic and farm animals by administering to said animals and anthelmintically effective amount of phosphonium compounds defined and graphically illustrated by structures I and II below:

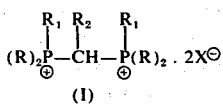

(I)

and

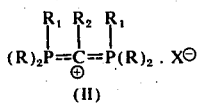

(II)

Wherein R is phenyl; $R_1$ is the radical

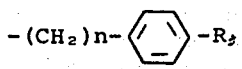

where $n$ is 0 or 1, $R_3$ is hydrogen or $C_1$–$C_3$ alkyl; $R_2$ is a member selected from the group consisting of hydrogen, halogen, $C_1$–$C_6$ alkyl, the radical

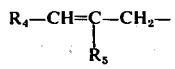

where $R_4$ and $R_5$ may be the same or different and are selected from hydrogen or $C_1$–$C_3$ alkyl, the radical $R_6$—S—$CH_2$— where $R_6$ is $C_1$–$C_4$ alkyl, or the radical

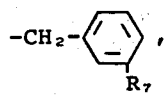

where $R_7$ is hydrogen or methoxy; ═ is a double or single bond, only one double bond being present at any time; $X^\ominus$ is a pharmacologically acceptable anion selected from the group consisting of acetate, propionate, gluconate, pamoate, phosphate, $Cl^\ominus$, $Br^\ominus$, $I^\ominus$,

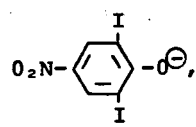

$Br^\ominus$. $FeCl_3$, or $Br^\ominus$. $CuBr_2$, and preferably selected from the group consisting of $Cl^\ominus$, $Br^\ominus$, $I^\ominus$,

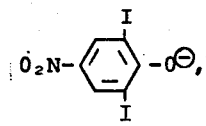

$Br^\ominus$. $FeCl_3$, or $Br^\ominus$. $CuBr_2$.

The above-described compounds are highly active when administered orally or by subcutaneous or intraruminal injection to domestic or farm animals and are effective against a wide variety of helminths, including the genera Haemonchus, Osteragia, Trichostrongylus, Cooperia, Nematodirus, Oesophagostomum, and Trichuris.

The chemistry, preparation and agricultural use of compounds represented by types (I) and (II) below:

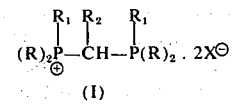

(I)

and

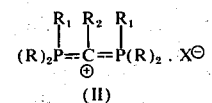

(II)

Wherein R, $R_1$, $R_2$ and $X^\ominus$ are defined as above, is amply documented in the literature [e.g. Angewandte Chemie, 71: 261–273, (1959); Journal of the American Chemical Society, 83: 3539–40, (1961); Journal of the American Chemical Society, 89: 6273–76, (1967); Journal of Organic Chemistry, 29: 2427–31; (1964)] and in a number of U.S. Pats. (e.g. Nos. 2,912,467; 3,262,971; 3,374,256; 3,437,473).

The pronounced anthelmintic activity of phosphonium compounds of type (I) and (II) is unexpected, not obvious to one familiar with the prior art, since the literature articles make no mention of any biological activity against helminths nor do the authors anticipate, predict or even imply such activity. Clearly the Patents cited assign to such compounds herbicidal, fungicidal, defoliant, larvicidal, nematocidal activities and the like for intended use in the field of agriculture for the protection of commercially useful plant crops against bacteria, fungi, nematodes and the like.

The textbook, "Principles of Nematology" [by: G. Thorne, McGraw-Hill Book Company Inc. (1961)] refers to USAD scientist N.A. Cobb, who was the first to propose: that plant parasitic and free-living nematodes be removed from helminthology and be assigned to a new branch of science to be known as "Nematology" (Chapter 1, page 14, paragraph 3). The same book, in the same Chapter, on page 5 makes a reference to the fact, that the branch of science, under which animal parasitic forms of nematode are studied, became known as "helminthology" since the Nineteenth Century. Thus the term "nematode" is used to describe those free living members of the genus Nematoda which parasitize plant crops, and is so used. Nor is the term "Nematode commonly used to describe helminths of the genus Nematoda parasitizing domestic and farm animals. Further, nematocides employed to control nematodes of crops are not as a general rule employed to control helminths parasitizing domestic and farm animals. The domestic and farm animals are, for example, cattle, swine, sheep, goats, dogs and cats. Thus the anthelminthic activity of phosphonium compounds of types (I) and (II) is unexpected, and novel.

It has been found that effective helminth control can be achieved in domestic and farm animals when a compound defined by structure (I) and (II) above is administered to said animals in a single dose at dosage levels of from 1 mg./kg. to 200 mg./kg. of animal body weight, and preferably between 7.5 mg./kg. to 30 mg./kg. of animal body weight.

Advantageously, the compounds defined by structures (I) and (II) above can also be administered to domestic and farm animals on a continuing basis incorporated in the diet of the animals at drug levels between 0.006 and 0.2% by weight of the feed, and preferably between 0.0125 and 0.025% by weight of the feed. For incorporation in the feed, the active compound may be formulated as a premix or supplement containing from about 5 to 25% by weight of drug. The remainder of the premix or supplement is usually a mixture of animal nutrients, e.g. soybean meal, ground grain, corn meal, fermentation residues, vegetable oils and the like. The premix or supplement is added to the animal feed in sufficient amount to provide the drug concentration required for controlling the helminth infection of said animals.

For single dose administration the compounds may be formulated as boluses, tablets, pills, injectables and the like, using pharmaceutically acceptable diluents, binders, lubricants, solvents and the like, e.g. dicalciumphosphate, starch, lactose, magnesium stearate, vegetable gums, isotonic saline solution and the like.

SPECIFIC DISCLOSURE

The following examples are given to illustrate the method of invention for controlling helminths by the use of phosphonium compounds of the types (I) and (II), as defined above.

EXAMPLE 1

Evaluation (Efficacy) Test in Mice

The primary target parasite of this test is *Nematospiroides dubius* (Family: Heligmosomidae), which is phylogenetically related to certain economically important parasites of domestic and farm animals. Mice are orally inoculated with 20 to 30 infective *N. dubius* larvae. Mixed infections are obtained by subsequent inoculation with *Aspicularis tetraptera* and *Hymenolepis nana*. Eighteen days after inoculation the mice are divided into groups of four. Each group receives one compound at a specified dose rate, either as a single gavage dose or fed continually in the feed. Four groups of five mice each are utilized as infected, untreated controls. For those mice receiving continual treatment, the compounds are mixed in the diet at drug levels of 0.006 to 0.1% by weight of feed and are fed for 7 days, initiated 18 days after inoculation. Those mice receiving single oral doses (SOD) or a single subcutaneous injection (Sc) of 5 mg./kg. to 100 mg./kg. of animal body weight of the compound under test are treated 22 days after inoculation. Eight days after start of treatment (drug diet) and 4 days post treatment (single dose SOD or Sc), the mice are necropsied, the worms recovered and counted. Percent efficacy for Nematospiroides is calculated using the formula: % Efficacy Equals $$\frac{\text{Avg. no. of worms in Control - Avg. no. of worm in treated}}{\text{Avg. no. of worms in Control}} \times 100$$

Tapeworm and pinworm efficacy is determined by the presence or absence of worms in each treated mouse.

The diet used in the test procedures is a standard commercial mouse chow containing meat and bone meal, dried skimmed milk, wheat germ meal, fish meal, animal liver meal, dried beet pulp, ground extended corn, oat middlings, soybean meal, dehydrated alfalfa meal, cane molasses, animal fat preserved with BHA, vitamin B-12 supplement, calcium panthotenate, choline chloride, folic acid, riboflavin supplement, brewer's dried yeast, thiamine, niacin, vitamin A supplement, D activated plant sterol, vitamin E supplement, dicalcium phosphate, iodized salt, ferric ammonium citrate, iron oxide, manganous oxide, cobalt carbonate, copper oxide and zinc oxide; and the desired level of test compound.

When the drug is administered as a single oral dose, the drug is weighed and suspended in 0.2% agar, thoroughly mixed and orally introduced at the required volume.

The experimental dosage and results are summarized in Table I, II and III below.

Table I

Anthelmintic Activity of Type I Compounds in Mice $$(R)_2\overset{+}{P}-\underset{\underset{R_2}{|}}{C}H-\overset{+}{P}(R)_2 \cdot 2X^{\ominus}$$  Wherein $R_2$ is hydrogen and R is phenyl

| $R_1$ | X | Drug Diet | | | Single Oral Dose | | | Subcutaneous | | |
|---|---|---|---|---|---|---|---|---|---|---|
| | | % Diet | % Eff.N.d. | No. Mice | mg/kg | % Eff.N.d. | No. Mice | mg/kg | % Eff.N.d. | No. Mice |
| Phenyl | Cl | 0.0125 | 100* | 4 | 25 | 96.5 | 7 | | | |
| | | 0.006 | 85 | 4 | 10 | 84 | 4 | | | |
| | | | | | 5 | 85 | 4 | | | |
| Phenyl | Br | 0.025 | 100* | 4 | 25 | 95.5 | 8 | 25 | 84 | 4 |
| | | 0.125 | 94* | 4 | 10 | 51.5 | 8 | 10 | 42 | 4 |
| | | 0.006 | 78 | 4 | 5 | 49 | 4 | | | |
| p-tolyl | Br | 0.1 | 57 | 4 | 100 | 75 | 4 | | | |
| | | | | | 50 | 57 | 4 | | | |
| One is phenyl | Br | 0.05 | 80* | 4 | 100 | 77 | 3 | | | |
| One is p-tolyl | | 0.025 | 60 | 4 | 50 | 64 | 4 | | | |
| | | | | | 25 | 57 | 8 | | | |
| Benzyl | Br | 0.05 | 73 | 4 | 100 | 80* | 4 | | | |
| | | | | | 50 | 79 | 4 | | | |

N.d. = Nematospiroides dubius
*= Also active against Aspicularis tetraptera
% Eff. = % Efficacy

Table II

Anthelmintic Activity of Type II Compounds in Mice $$(R)_2\overset{+}{P}=\overset{R_1\ R_2\ R_1}{\underset{|\ \ \ |\ \ \ |}{C}}=P(R)_2 \cdot X^{\ominus}$$

Wherein $R_2$ is hydrogen and R is phenyl

| $R_1$ | X | Drug Diet | | | Single Oral Dose | | | Subcutaneous | | |
|---|---|---|---|---|---|---|---|---|---|---|
| | | % Diet | % Eff. N.d. | No. Mice | mg/kg | % Eff. N.d. | No. Mice | mg/kg | % Eff. N.d. | No. Mice |
| Phenyl | Br | 0.0125 | 100* | 3 | 25 | 89 | 11 | 25 | 94 | 4 |
| | | 0.006 | 94 | 4 | 10 | 65 | 12 | 10 | 74 | 4 |
| | | | | | 5 | 32.5 | 8 | | | |
| Phenyl | Cl | 0.0125 | 100* | 4 | 25 | 96 | 7 | | | |
| | | 0.006 | 91 | 4 | 10 | 51 | 7 | | | |
| Phenyl | I | 0.0125 | 100 | 4 | 25 | 91 | 10 | | | |
| | | 0.006 | 89 | 4 | 10 | 67 | 12 | | | |
| | | | | | 5 | 26 | 12 | | | |
| Phenyl | Br⁻.FeCl₃ | 0.0125 | 100* | 4 | **25 | 96 | 4 | | | |
| | | | | | **10 | 54 | 4 | | | |
| | | | | | ** 5 | 45 | 4 | | | |
| Phenyl | Br⁻.CuBr₂ | 0.025 | 100 | 4 | **25 | 76 | 4 | | | |
| | | 0.0125 | 51 | 4 | **10 | 43 | 4 | | | |
| Phenyl | | 0.0125 | 100 | 4 | **25 | 94 | 4 | | | |
| | | 0.006 | 85 | 4 | **10 | 63 | 4 | | | |
| | | | | | ** 5 | 49 | 4 | | | |
| Phenyl | 2,6-Diiodo-4-nitrophenol | 0.025 | 99.5 | 8 | **25 | 88.5 | 16 | | | |
| | | 0.0125 | 86.5 | 8 | **10 | 44.7 | 16 | | | |
| | | 0.006 | 41 | 4 | ** 5 | 36.7 | 16 | | | |
| p-tolyl | Br | 0.1 | 53* | 8 | 100 | 89 | 3 | | | |
| | | | | | 50 | 36 | 4 | | | |
| One is Phenyl, One is p-tolyl | CH₃-C₆H₄-SO₃⁻ | | | | | | | | | |
| | Br | 0.1 | 67 | 4 | 100 | 67 | 4 | | | |
| | | 0.05 | 59 | 8 | 50 | 31 | 4 | | | |

N.d. = Nematospiroides dubius
* = Also active against Aspicularis tetraptera
** = Dosage weight is that of the cation
% Eff = % Efficacy

Table III

Anthelmintic Activity of Type II Compounds in Mice $$(R)_2\overset{+}{P}=\overset{R_1\ R_2\ R_1}{\underset{|\ \ \ |\ \ \ |}{C}}=P(R)_2 \cdot X^{\ominus}$$

Wherein both R and $R_1$ are phenyl

| $R_2$ | X | Drug Diet | | | Single Oral Dose | | | Subcutaneous | | |
|---|---|---|---|---|---|---|---|---|---|---|
| | | % Diet | % Eff.N.d. | No. Mice | mg/kg | % Eff.N.d. | No. Mice | mg/kg | % Eff.N.d. | No. Mice |
| Methyl | I | 0.0125 | 99 | 4 | 25 | 98* | 20 | 25 | 100 | 6 |
| | | 0.006 | 98 | 4 | 10 | 96* | 20 | 10 | 95 | 8 |
| | | 0.003 | 57 | 4 | 5 | 65 | 20 | 5 | 80 | 8 |
| Ethyl | I | 0.025 | 100 | 4 | 50 | 85* | 4 | | | |
| | | 0.0125 | 74 | 4 | 25 | 75 | 4 | | | |
| | | 0.006 | 46 | 4 | 10 | 68 | 4 | | | |
| n-Propyl | I | 0.025 | 100 | 4 | 50 | 100 | 3 | | | |
| | | 0.0125 | 88 | 4 | 25 | 63 | 4 | | | |
| | | 0.006 | 86 | 4 | 10 | 42 | 4 | | | |
| | | 0.003 | 50 | 4 | | | | | | |
| n-Hexyl | Br | 0.025 | 100 | 4 | 100 | 94 | 2 | | | |
| | | 0.0125 | 79 | 3 | 50 | 61 | 7 | | | |
| | | 0.006 | 58 | 4 | 25 | 39 | 4 | | | |
| Allyl | Br | 0.025 | 100 | 4 | 50 | 100 | 4 | | | |
| | | 0.0125 | 33 | 4 | 25 | 86 | 4 | | | |
| | | | | | 10 | 60 | 4 | | | |
| CH₃—S—CH₂— | Cl | 0.1 | 97 | 4 | | | | | | |
| | | 0.05 | 65 | 8 | | | | | | |
| | | 0.025 | 56 | 8 | | | | | | |
| Benzyl | Br | 0.05 | 100* | 4 | 50 | 100* | 4 | | | |
| | | 0.025 | 96 | 8 | 25 | 72 | 4 | | | |
| | | 0.0125 | 89 | 4 | | | | | | |
| m-methoxy-benzyl | Cl | 0.05 | 100* | 4 | 100 | 76 | 12 | | | |
| | | 0.025 | 88 | 8 | 50 | 58 | 12 | | | |
| | | 0.0125 | 58 | 4 | | | | | | |
| Br | Br | 0.025 | 100 | 4 | 50 | 100 | 8 | | | |
| | | 0.0125 | 88 | 4 | 25 | 83 | 8 | | | |
| | | | | | 10 | 67 | 8 | | | |
| I | I | 0.025 | 100* | 4 | | | | | | |
| | | 0.0125 | 98 | 4 | 50 | 70 | 4 | | | |
| | | 0.006 | 54 | 4 | | | | | | |

N.d. = Nematospiroides dubius
* = Also active against Aspicularis tetraptera
% Eff. = Efficacy

EXAMPLE 2

Evaluation (Efficacy) Test in Sheep

Lambs of mixed breeding are experimentally inoculated with *Ostertagia circumcincta* and Trichostrongylus species. At patency of the parasites the lambs are treated with 7.5 mg./kg. to 30 mg./kg. body weight of the animal with the compound under test, administered as a single oral dose (OD) or intraruminal injection (IR) in 0.2% agar. After treatment, 24 hour fecal outputs for 3 days are collected from each animal and examined for the passage of parasites. Three days post treatment the lambs are necropsied and examined for parasites. Percent efficacy is calculated using the formula:

$$\% \text{ Efficacy} = \frac{\text{No. of parasites passed}}{\text{No. passed + No. retained}} \times 100$$

The dosage, mode of treatment and % efficacy obtained in this experiment are summarized in Table IV below.

Table IV

| Compound | mg/kg Dose | Mode of Treatment | % Efficacy T. spp. | O.c. |
|---|---|---|---|---|
| 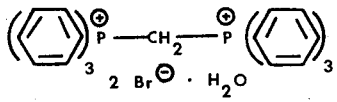 | 15 | OD | 77 | 92 |
| | 15 | OD | 99 | 61 |
| | 15 | IR | * | 91 |
| | 15 | IR | 71 | 86 |
| | 7.5 | OD | 87 | 49 |
| | 7.5 | OD | 80 | 32 |
| 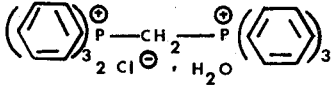 | 30$^a$ | OD | 99 | 96 |
| 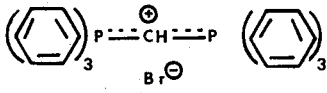 | 15 | OD | 99 | 94 |
| | 15 | OD | 76 | 69 |
| | 15 | IR | * | 96 |
| | 15 | IR | * | 93 |
| | 7.5 | OD | 37 | 30 |
| | 7.5 | OD | 95 | 38 |

$^a$ = Intoxication observed
\* = Insufficient worms present
T.spp. = Trichostrongylus species
O.c. = Ostertagia circumcincta

EXAMPLE 3

Evaluation (Efficacy) Test in Sheep

In this example the efficacy of phosphonium compounds of type (I) and (II) against a wide variety of helminths are evaluated in naturally infected sheep. A controlled test is used. Groups of test and control animals with similar mean worm population and the same range of variation in individual populations are selected by using appropriate egg counting methods. The data are summarized in Table V below.

Table V

| Compound | mg/kg dose | Efficacy in Sheep No. of Sheep | H.c. | O.c. | T.a. | T.c. | C.spp. | % Efficacy N | Bun. | Oes. | Ch. | T.o. |
|---|---|---|---|---|---|---|---|---|---|---|---|---|
| 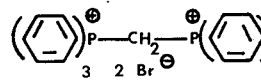 | 15 | 4 | 80 | 96 | 95 | 98 | 99 | 99 | 33 | 82 | 0 | — |
| | 30 | 4 | 81 | 99 | 99 | 100 | 100 | 100 | 0 | 80 | 20 | — |
| 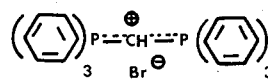 | 7.5 | 4 | 42 | 62 | — | 47 | — | 100 | — | — | — | 62 |
| | 15 | 4 | 52 | 94 | 99 | 99 | 99 | 99 | 0 | 54 | 0 | — |
| | 15$^a$ | 4 | 18 | — | 84 | 99 | 99 | 99 | — | — | — | — |
| 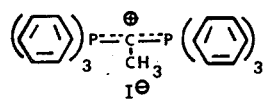 | 7.5 | 4 | 53 | 86 | — | 71 | — | 100 | — | — | — | 59 |
| | 15 | 4 | 85 | 98 | — | 99 | — | 100 | — | — | — | 88 |
| | 30 | 4 | 84 | — | 95 | 100 | 100 | 100 | — | — | — | — |
| 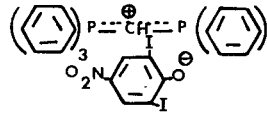 | 15$^a$ | 4 | 100 | — | 76 | 100 | 100 | 97 | — | — | — | — |

Table V-continued

| Compound | mg/kg dose | Efficacy in Sheep No. of Sheep | H.c. | O.c. | T.a. | T.c. | C.spp. | % Efficacy N | Bun. | Oes. | Ch. | T.o. |
| --- | --- | --- | --- | --- | --- | --- | --- | --- | --- | --- | --- | --- |
| Infected, untreated groups, average number of worms found in group | group 1 | 4 | 1594 | 6340 | 2842 | 6392 | 3525 | 1350 | 12 | 106 | 30 | 8 |
| | grous 2 | 4 | 2331 | 2094 | 0 | 4742 | 0 | 142 | 0 | 0 | 0 | 37 |
| | group 3 | 6 | 742 | 0 | 62 | 156 | 238 | 980 | 0 | 0 | 0 | 4.5 |

*a* = Phosphonium base
H.c. = Haemonchus contortus; O.c. = Ostertagia circumcincta; T.a = Trichostrongylus axei; T.c. = Trichostrongylus colubriformis; C.spp. = Cooperia species; N = Nematodirus; Bun. = Bunostomum; Oes. = Oesophagostomum; Ch. = Chabertia; T.o. = Trichuris ovis The following examples are given for the purpose of illustrating the preparation of representative anthelmintically active compounds of types (I) and (II).

EXAMPLE 4

Preparation of Methylenebis Triphenylphosphonium Dibromide

Triphenylphosphine (26.2 g., 0.1 mole), dibromomethane (3.48 ml., 0.05 mole) and triphenylphosphate are mixed, stirred and heated under a nitrogen atmosphere at 85°C. to 95°C. for 4 hours and then at 140°C. to 145°C. overnight. The reaction mixture is added to benzene and the supernatant decanted. The residue is stirred with ethyl acetate and the resulting solid filtered. The solid is mixed with acetone and the mixture stirred overnight. The solid is filtered and recrystallized from a mixture of chloroform/ethyl acetate and is dried under reduced pressure.

EXAMPLE 5

Preparation of Methylenebis(diphenyl-p-tolyl) Phosphonium Dibromide

The above compound is prepared by the procedure of Example 4 by substituting diphenyl-p-tolylphosphine for triphenylphosphine. The melting point of the compound is 316°C. to 320°C.

EXAMPLE 6

Preparation of P,P,P,P',P'-Pentaphenyl P'-p-tolyl-P,P' Methylenediphosphonium Dibromide Bromomethyltriphenylphosphonium bromide (21.8 g., 0.05 mole), diphenyl-p-tolylphosphine (15.2 g., 0.055 mole) and triphenylphosphate (50 g.) are mixed, stirred and heated at 140°C. under a nitrogen atmosphere for 72 hours. The reaction mixture is allowed to cool, and is slurried with benzene. The supernatant is decanted, the residue slurried with ethyl acetate and filtered. The solid becomes oily, is reslurried with heating in acetone, the resulting solid is filtered and recrystallized from a mixture of chloroform/ethyl acetate. The crystalline solid is dried under reduced pressure to give the above product as the dihydrate, melting point 301°C. to 304°C.

EXAMPLE 7

Preparation of Methylenebis(benzyldiphenyl)phosphonium Dibromide

Methylenebis diphenylphosphine (7.7 g., 0.02 mole) and benzylbromide (14.4 g., 0.084 mole) are mixed and stirred at room temperature. The reaction is exothermic and on cooling a solid mass forms. Toluene (25 ml.) is added and the mixture is heated at reflux overnight. The reaction mixture is filtered and washed with benzene to yield 11.5 g. of solid, m.p. 235°C. to 242°C. This solid is dissolved in methanol (50 ml.) and then ethyl acetate (200 ml.) is added. The solution is concentrated, and the solid filtered and dried to yield 2.2 g. of methylenebis(benzyldiphenyl)phosphonium dibromide, melting point 291°C. to 294°C.

EXAMPLE 8

Preparation of Triphenyl[(triphenylphosphoranylidene)methyl]- phosphonium Bromide Sodium carbonate (12.7 g., 0.12 mole) is dissolved in water (150 ml.). Methylenebis triphenylphosphonium dibromide (14.3 g., 0.02 mole) is added and the mixture stirred and heated at reflux 5 hours. The reaction mixture is cooled and filtered. The isolated solid is washed with water, recrystallized from a mixture of methanol/ethyl acetate and dried under reduced pressure to yield 9.8 g. of triphenyl[(triphenylphosphoranylidene)methyl]phosphonium bromide, melting point 270°C. to 272°C.

EXAMPLE 9

Preparation of Triphenyl[(triphenylphosphoranylidene)methyl]- phosphonium Chloride The above product is prepared by the procedure of Example 8 by substituting methylenebis triphenylphosphonium dichloride for the dibromide described in said reaction.

EXAMPLE 10

Preparation of Triphenyl[(triphenylphosphoranylidene)methyl]- phosphonium Iodide The above product is prepared by the procedure of Example 8 by substituting methylenebis triphenylphosphonium diiodide for the dibromide mentioned in said example.

EXAMPLE 11

Preparation of Triphenyl[(triphenylphosphoranylidene)methyl]- phosphonium Bromide, Compound with Ferric Chloride Anhydrous ferric chloride (1.32 g., 0.0081 mole) and methylenedichloride (150 ml.) are mixed and triphenyl[(triphenylphosphoranylidene)methyl]bromide (5.0 g., 0.008 mole) is added under a nitrogen atmosphere. The reaction mixture is stirred overnight at room temperature. The reaction mixture is then filtered, the filtrate evaporated to dryness. Ethanol (200 ml.) is added to the residue, the mixture is stirred, filtered, the isolated solid washed with ethanol and dried under reduced pressure. Yield 5.9 9. triphenyl[(-triphenylphosphoranylidene)-methyl]phosphonium bromide compound with ferric chloride, m.p. 227°C. to 228°C.

EXAMPLE 12

Preparation of Triphenyl[(triphenylphosphoranylidene)methyl]-phosphonium Bromide, Compound with Cupric Chloride The above compound is prepared by the procedure of Example 11 by substituting cupric chloride for ferric chloride.

EXAMPLE 13

Preparation of Triphenyl[(triphenylphosphoranylidene)methyl]-phosphonium-2,6-diiodo-4-nitrophenolate 2,6-Diiodo-4-nitrophenol (3.91 g., 0.01 mole) is added to a suspension of hexaphenylcarbodiphosphorane (5.37 g., 0.01 mole) in benzene (150 ml.) under a nitrogen atmosphere. The reaction mixture is stirred at room temperature overnight then at reflux for 3 hours. The reaction mixture is filtered, the isolated solid washed and dried. The crude product, m.p. 140°C. to 142°C. is recrystallized from a mixture of chloroform/heptane and dried under reduced pressure to yield triphenyl[(triphenylphosphoranylidene)methyl]phosphonium-2,6-diiodo-4-nitrophenolate.

EXAMPLE 14

Preparation of Triphenyl[(triphenylphosphoranylidene)methyl]-phosphonium-p-toluenesulfonate The above compound is prepared by the procedure of Example 13 by substituting p-toluenesulfonic acid for 2,6-diiodo-4-nitrophenol.

EXAMPLE 15

Preparation of Triphenyl[1-(triphenylphosphoranylidene)ethyl]-phosphonium Iodide Methyl iodide is added to a stirred suspension of hexaphenylcarbodiphosphorane (5.37 g., 0.01 mole) in dry benzene (50 ml.) under a nitrogen atmosphere. The reaction mixture is stirred at room temperature for 72 hours.

The reaction mixture is filtered, the isolated solid washed with benzene and ether. It is then recrystallized from a mixture of ethanol/ethyl acetate to yield triphenyl[1-(triphenylphosphoranylidene)ethyl]phosphonium iodide, m.p. 270°C. to 272°C.

EXAMPLES 16–20

The procedure of Example 15 is followed to prepare compounds of the type:

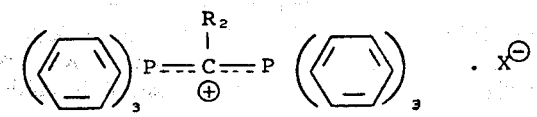

wherein $R_2$, X and melting points are as follows:

| $R_2$ | X | Melting Point |
|---|---|---|
| ⟨phenyl⟩-CH$_2$- | Br | 274°C. to 278°C. |
| CH$_3$CH$_2$- | I | 292°C. to 294°C. |
| n-C$_3$C$_7$ | I | 284°C. to 287°C. |
| n-C$_6$H$_{11}$- | Br | 209°C. to 211°C. |
| ⟨phenyl, OCH$_3$⟩-CH$_2$- | Cl | 208°C. to 212°C. |

EXAMPLE 21

Preparation of Triphenyl[1-(triphenylphosphoranylidene)allyl]-phosphonium Bromide Allylbromide (3.63 g., 0.03 mole) is added to a stirred solution of (hexaphenylcarbodiphosphorane) (5.37 g., 0.01 mole) in benzene (150 ml.) under a nitrogen atmosphere. The reaction mixture is stirred at room temperature overnight, then heated at reflux for 4 hours. The reaction mixture is then cooled to room temperature, filtered, the isolated solid is washed with benzene, yield 4.45 g., m.p. 250°C. to 257°C. The crude product is recrystallized from a mixture of methanol/ethyl acetate to yield pure triphenyl[1-(triphenylphosphoranylidene)allyl]-phosphonium bromide, m.p. 260°C. to 262.5°C.

EXAMPLE 22

The procedure of Example 21 is followed to prepared compounds of the type:

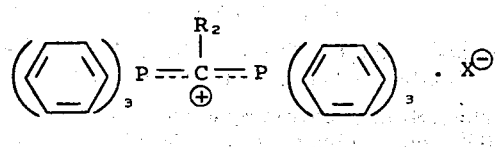

wherein $R_2$ and X are as follows:

| $R_2$ | X |
|---|---|
| CH$_3$-CH=CH-CH$_2$- | Br |
| CH$_2$=C(CH$_3$)-CH$_2$- | Br |
| CH$_3$-CH=C(CH$_3$)-CH$_2$ | Br |
| CH$_3$CH$_2$-CH=CH-CH$_2$ | Br |
| CH$_2$=C(C$_2$H$_5$)-CH-CH$_2$ | Br |
| CH$_3$CH$_2$CH$_2$-CH=CH-CH$_2$ | Br |

EXAMPLE 23

Preparation of [2-(methylthio)-1-(triphenylphosphoranylidene)-ethyl]triphenylphosphonium Chloride Chloromethyl methylsulfide (1.93 g., 0.02 mole) is added to a stirred slurry of hexaphenylcarbodiphosphorane (5.4 g., 0.01 mole) in dry benzene (150 ml.). The mixture is stirred under a nitrogen atmosphere for 72 hours at room temperature. The reaction mixture is then heated at reflux overnight, filtered, the isolated solid washed with benzene to yield 4.5 g. crude product, m.p. 172°C. to 180°C. The crude is recrystallized from a mixture of acetone/ethyl acetate to yield pure [2-(methylthio)-1-(triphenylphosphoranylidene)ethyl]-triphenylphosphonium chloride, m.p. 245°C. to 248°C.

EXAMPLE 24

The procedure of Example 23 followed to prepared compounds of the type:

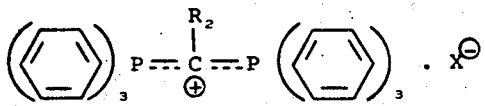

wherein $R_2$ and X are as follows:

| $R_2$ | X |
|---|---|
| $CH_3CH_2S—CH_2—$ | Cl |
| $CH_3CH_2CH_2S—CH_2—$ | Cl |
| $CH_3CH_2CH_2CH_2S—CH_2—$ | Cl |

EXAMPLE 25

Preparation of [Bromo(triphenylphosphoranylidene)methyl]phosphonium Bromide

Bromine (0.52 ml.) is added dropwise to a stirred solution of hexaphenylcarbodiphosphorane (5.37 g., 0.01 mole) in chlorobenzene (150 ml.) under a nitrogen atmosphere. The reaction mixture is stirred at room temperature overnight, then heated at reflux for 4 hours. The reaction mixture is then cooled to room temperature, filtered, the isolated solid washed with benzene and recrystallized from a mixture of methanol-/ethyl acetate and dried under reduced pressure, m.p. 260°C. to 263°C.

EXAMPLE 26

Preparation of [Iodo(triphenylphosphoranylidene)methyl]phosphonium Iodide

The above compound is prepared by the procedure of Example 25 by substituting iodine for bromine.

We claim:

1. A method for controlling helminths in a domestic and farm animal comprising administering orally, subcutaneously or intraruminally to said animal an anthelmintically effective amount of a phosphonium compound having a formula selected from the group consisting of:

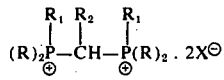

(I)

and

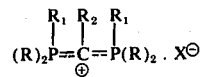

(II)

wherein R is phenyl; $R_1$ is the radical

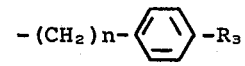

where n is 0 or 1, $R_3$ is hydrogen or $C_1$-$C_3$ alkyl; $R_2$ is a member selected from the group consisting of hydrogen, halogen, $C_1$-$C_6$ alkyl, and

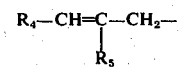

where $R_4$ and $R_5$ are selected from the group consisting of hydrogen, $C_1$-$C_3$ alkyl, $C_1$-$C_4$ alkyl—S—$CH_2$—,

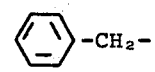

and

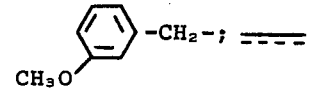

is a double or single bond, only one double bond being present at any time; $X^\ominus$ is a pharmacologically acceptable anion selected from the group consisting of acetate, propionate, gluconate, pamoate, phosphate, $Cl^\ominus$, $Br^\ominus$, $I^\ominus$,

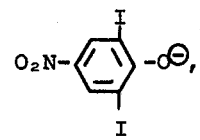

$Br^\ominus$. $FeCl_3$, and $Br^\ominus$, $CuBr_2$.

2. A method in accordance with claim 1, wherein the phosphonium compound is administered in a single dose of from 1 mg. to 200 mg. per kilogram of animal body weight.

3. The method in accordance with claim 1 wherein the phosphonium compound is triphenyl[1-(triphenylphosphonranylidene)ethyl]phosphonium iodide.

4. The method in accordance with claim 1 wherein the phosphonium compound is triphenyl[1-(triphenylphosphoranylidene)allyl]phosphonium bromide.

5. The method in accordance with claim 1 wherein the phosphonium compound is [bromo(triphenylphosphoranylidene)-methyl]phosphonium bromide.

6. The method in accordance with claim 1 wherein the phosphonium compound is the salt of triphenyl[(-triphenylphosphoranylidene)methyl]phosphonium cation with an anion selected from the group consisting of chlorine, bromine, iodine, p-toluenesulfonic acid and 2,6-diiodo-4-nitrophenol.

7. The method in accordance with claim 1 wherein the phosphonium compound is a compound of triphenyl[(triphenylphosphoranylidene)methyl]phosphonium bromide with ferric chloride.

8. The method in accordance with claim 1 wherein the phosphonium compound is the salt of methylenebis triphenylphosphonium cation with an anion selected from the group consisting of chloride and bromide.

9. A method in accordance with claim 1 wherein the phosphonium compound is triphenyl[1-(triphenylphosphoranylidene)-allyl]phosphonium bromide.

10. The method in accordance with claim 1 wherein the phosphonium compound is the salt of triphenyl[triphenylphosphoranylidene)methyl]phosphonium cation with an anion selected from the group consisting of chlorine, bromine, iodine, p-toluenesulfonic acid and 2,6-diiodo-4-nitrophenol.

11. The method in accordance with claim 1 wherein the phosphonium compound is a compound of triphenyl[(triphenylphosphoranylidene)methyl]phosphonium bromide with ferric chloride.

12. A method in accordance with claim 1 wherein the phosphonium compound is the salt of methylenebis triphenylphosphonium cation with an anion selected from the group consisting of chlorine and bromine.

13. The method in accordance with claim 1 wherein the phosphonium compound is the compound formed with cupric bromide.

14. The method in accordance with claim 1 wherein the phosphonium compound has the formula:

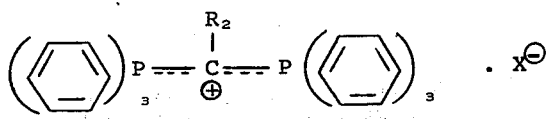

wherein $R_2$ is a member selected from the group consisting of iodine, ethyl, n-propyl-, n-hexyl-, methyl-thiomethyl, benzyl and m-methoxybenzyl; and X is a member selected from the group consisting of bromine, chlorine and iodine.

15. A method in accordance with claim 1 where the phosphonium compound is triphenyl[1-(triphenylphosphoranylidene)ethyl]phosphonium iodide.

16. The method in accordance with claim 1 wherein the phosphonium compound is [bromo(triphenylphosphoranylidene)methyl]phosphonium bromide.

17. The method in accordance with claim 1 wherein the phosphonium compound is a compound of triphenyl[(triphenylphosphoranylidene)methyl]phosphonium bromide with ferric chloride.

18. The method of claim 1 wherein the phosphonium compound has the formula:

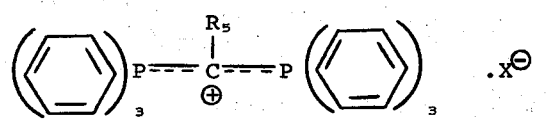

wherein $R_5$ is a member selected from the group consisting of iodine, ethyl, n-propyl-, n-hexyl-, methylthiomethyl, benzyl and m-methoxybenzyl; and X is a member selected from the group consisting of bromine, chlorine and iodine.

19. The method in accordance with claim 1, wherein the phosphonium compound is administered orally to said animal on a continuing basis incorporated in a nutritionally medicated, balanced diet at a dose level of from 0.006 to 0.2% by weight of the balanced diet.

* * * * *